_United States Patent_ [19]

Bowley et al.

[11] Patent Number: 4,919,533
[45] Date of Patent: Apr. 24, 1990

[54] METHOD FOR DETECTING DIAMONDS IN REMOTE LOCATIONS

[75] Inventors: Heather J. Bowley, Middlesex; Donald L. Gerrard, Surrey; John E. Preedy, Kent, all of England

[73] Assignee: The British Petroleum Company plc, London, England

[21] Appl. No.: 275,146

[22] PCT Filed: Mar. 10, 1988

[86] PCT No.: PCT/GB88/00187
§ 371 Date: Nov. 15, 1988
§ 102(e) Date: Nov. 15, 1988

[87] PCT Pub. No.: WO88/07213
PCT Pub. Date: Sep. 22, 1988

[30] Foreign Application Priority Data

Mar. 18, 1987 [GB] United Kingdom ................. 8706421

[51] Int. Cl.⁵ .................. G01V 9/04; G01N 21/65
[52] U.S. Cl. ........................ 356/30; 356/301
[58] Field of Search ................... 356/30, 301

[56] References Cited

U.S. PATENT DOCUMENTS 3,371,574 3/1968 Dwyer ............................. 356/301
4,573,761 3/1986 McLachlan et al. ............ 350/96.24

FOREIGN PATENT DOCUMENTS 2517631 7/1976 Fed. Rep. of Germany .
2702332 1/1980 Fed. Rep. of Germany .
2540682 2/1986 Fed. Rep. of Germany .
2571144 4/1986 France .............................. 356/301
2140555 11/1984 United Kingdom .
58-108438 6/1983 Japan .
8607457 12/1986 PCT Int'l Appl. ................ 356/301
8706011 10/1987 PCT Int'l Appl. .

OTHER PUBLICATIONS

G. D. Ferguson, "Blue Green Lasers for Underwater Applications", _Oceanoptics_, SPIE vol. 64 (1975) pp. 150–156.
G. Grasseli et al. "Use of Raman Spectrography in Chemistry", Moscow MIR 1984, pp. 186–187.
S. Schwab et al, "Versatile, Efficient Raman Sampling with Fiber Optics," Anal. Chem. 1984, 56, pp. 2199–2204.

_Primary Examiner_—F. L. Evans
_Attorney, Agent, or Firm_—Larry W. Evans; Joseph G. Curatolo

[57] ABSTRACT

A method for detecting diamonds in locations which are not easily accessible comprises irradiating material suspected of containing diamonds by means adapted for access to the location, collecting the resultant scattered Raman radiation by means adapted for access to the location and filtering and sensing the radiation to produce a signal whenever radiation characteristic of diamonds is sensed whereby the absence or the presence of diamonds in the location is indicated.

15 Claims, 3 Drawing Sheets

METHOD FOR DETECTING DIAMONDS IN REMOTE LOCATIONS

This invention relates to a detection method and more particularly relates to a method for detecting diamonds in locations which are not easily accessible.

It is often useful, for example when prospecting a site for diamond bearing ores, to examine samples of material to determine whether they contain diamonds. Such examination may be time consuming if samples have to be removed from the site and examined in a laboratory by conventional means. The examination may be further delayed if the material to be sampled is in a location which is not easily accessible.

Raman spectroscopy may be used for the separation of diamonds from a diamondiferous material and is disclosed in our UK patent no. GB 2140555B. The Raman signal of diamond is stronger than that of most other materials because diamond only contains carbon to carbon bonding and its Raman signal occurs at a position well separated from those of other minerals. Also, because diamond only contains one type of carbon to carbon bond, there is only a single Raman signal, which is readily distinguishable from associated broad band fluorescence. This means that the use of Raman spectroscopy is particularly suitable for detecting diamonds. The present invention relates to a further development of Raman spectroscopy which is suitable for detecting diamonds in locations which are not easily accessible.

Thus, according to the present invention there is provided a method for detecting diamonds in locations which are not easily accessible, the method comprising (a) irradiating material suspected of containing diamonds in a location which is not easily accessible, with laser radiation at a pre-determined wavelength, the irradiating means being adapted for access to the location and the laser radiation being capable of causing Raman radiation to be scattered from diamonds in the material, (b) collecting the scattered Raman radiation by a collecting means adapted for access to the location, (c) passing the collected Raman radiation through a filtering means adapted to pass only Raman radiation characteristic of diamonds, and (d) sensing the filtered Raman radiation by a sensing means adapted to produce a signal whenever radiation characteristic of diamonds is sensed, whereby the absence or the presence of diamonds in the location is indicated.

A device for irradiating the material with laser radiation may be a probe comprising a bundle of optical fibres which may be used to conduct the laser radiation from a laser to the material in locations which are not easily accessible, for example in crevices or down bore holes and the like. The collecting means may also be a probe comprising a bundle of optical fibres which may be used to conduct the scattered Raman radiation from the material to the filtering means. The optical fibres, which conduct the radiations to and from the location, may take the form of an integral flexible probe which may be pushed into crevices in the material or lowered down a bore hole.

Preferably the laser radiation is monochromatic and most preferably has a wavelength in the range 450 to 650 nanometers. The filtering means is preferably a narrow band pass filter and may comprise a thin glass slide having a suitable filter coating. The sensing means for the filtered Raman radiation may be based on a photocell but other forms of sensor may also be used, for example a photomultiplier tube, a diode array, a video camera, charge couple device camera, or a human eye.

It is envisaged that the apparatus used for the method according to the invention may be portable. Thus, the apparatus may be mounted on a lorry, jeep or other vehicle or may be sufficiently portable to be carried by an operator. The apparatus may be sufficiently compact to allow it to be lowered down a borehole or the like.

It is further envisaged that the apparatus may be mounted on a remote-controlled vehicle.

It is envisaged that the present invention may be used for subsea prospecting. The scattered Raman radiation in this case may be collected and filtered by a lens filter on a video camera, which sends a signal to a remote monitor on a surface vessel. Alternatively, the scattered Raman radiation may be passed to the filter and sensing means on the vessel through optical fibres. In this application if the sea water is muddy the region in front of the probe may be flushed with a supply of clean water or air. A pulsed illumination/reception system may also be used to reduce back scatter.

The invention also includes diamonds whenever detected by the method as hereinbefore described.

The invention will now be described by way of example only and with reference to the accompanying drawings.

Figure 1:
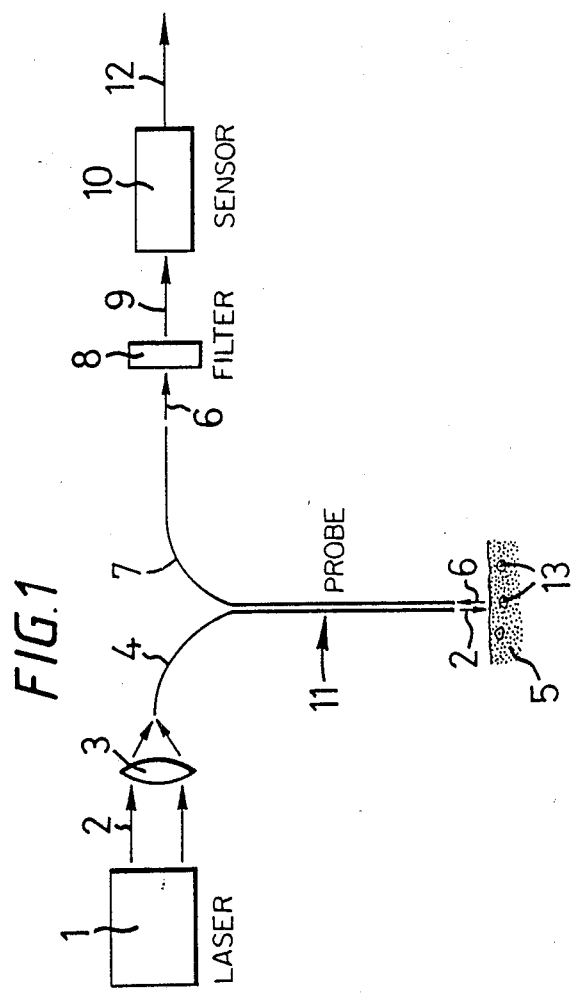
FIG. 1 illustrates, in schematic form, an apparatus for use in a method for detecting diamonds in locations which are not easily accessible according to the present invention.

In FIG. 1, the apparatus comprises a helium/neon gas type laser (1) adapted to produce laser radiation (2) of wavelength near 632.8 nanometers. A lens (3) is adapted to focus the laser radiation (2) into one or more light-conducting optical fibres (4). The optical fibres (4) form part of a probe (11) adapted for access to locations which are not easily accessible. The probe (11) also comprises one or more optical fibres (7) adapted to collect scattered Raman radiation (6) from diamonds (13) in the location which is not easily accessible. The collecting optical fibres (7) are adapted to pass the Raman radiation (6) to a narrow band pass filter (8) which is adapted to pass only scattered Raman radiation having a wavelength about 691.1 nanometers (a wavelength characteristic of diamond). A sensor (10) is adapted to sense the filtered radiation (9) and is adapted to produce a signal (12) whenever radiation characteristic of diamonds is sensed, whereby the absence or the presence of diamonds in the location is indicated.

In use, a material (5) suspected of containing diamonds (13) in a location which is not easily accessible is irradiated with laser radiation (2) of wavelength about 632.8 nanometers. The laser radiation (2) is produced by the laser (1) and is focused by lens (3) into the optical fibres (4) which form part of the probe (11) adapted for access to the location. The laser radiation (2) is capable of causing Raman radiation (6) to be scattered from diamonds (13) in the material (5). The scattered Raman radiation (6) is collected by optical fibres (7) which also form part of the probe (11) adapted for access to the location. The collecting optical fibres (7) pass the scattered Raman radiation (6) to the filter (8)

which passes only radiation having a wavelength of about 691.1 nanometers. The filtered Raman radiation (9) is sensed by the sensor (10) which produces a signal (12) whenever radiation characteristic of diamonds is sensed, whereby the absence or the presence of diamonds (13) in the location is indicated.

Figure 2:
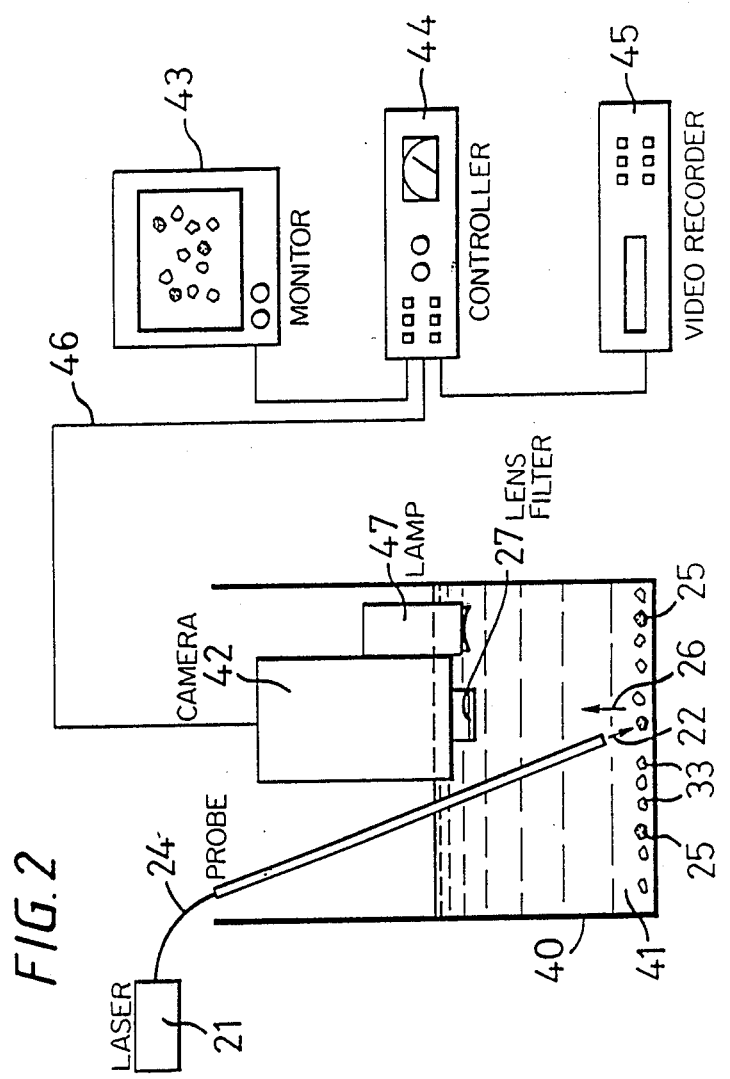
FIG. 2 illustrates, in schematic form, an apparatus used for detecting diamonds on a sea bed.

To demonstrate the feasibility of using the method according to the present invention to detect diamonds in a sea bed type environment, the apparatus shown in FIG. 2 was used. The apparatus comprised an argon ion laser (21) capable of producing laser radiation (22) having a wavelength of 514.5 nanometers. The laser radiation was passed along a fibre optic probe (24) with a tip power of approximately 200 mW. A 25 liter polythene container (40) was half-filled with sea water (41). Three diamond particles (25) were placed amongst a handful of non-diamond particles (33) scattered on the base of the container (40). Scattered Raman radiation (26) from the diamonds (25) was collected and filtered by the lens filter (27) of an Osprey underwater colour camera (42). The filter (27) had a wavelength cut off of 520 nanometers, that is it only passed radiation having a wavelength greater than 520 nanometers. The camera (42) with its lens filter (27) could be lowered into the seawater (41) in the tank (40). The camera (42) was capable of sensing the filtered radiation (not shown) and sending a signal (not shown) to a video monitor (43) outside the tank (40) along a cable (46) via a controller (44). A video recorder (45) was also provided. Normal visible light was provided to the tank (40) by a lamp (47).

In use the laser radiation was passed along the probe (24) and this was moved around the tank (40) to irradiate the particles (33) (25) on the base. Scattered Raman radiation (26) was collected and filtered by the lens filter (27) and sensed by the camera (42) which sent a signal to the video monitor (43).

Figure 3:
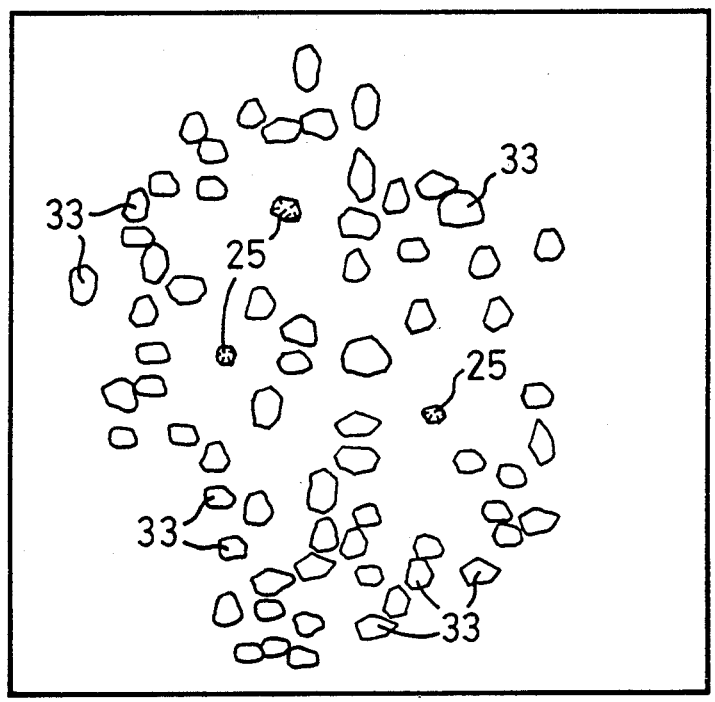
FIG. 3 shows, in schematic form, the image on the video monitor of the apparatus in FIG. 2.

A bright glow was seen on the video monitor (43) at the positions of the diamonds (25) indicating their presence. The image on the video monitor (43) is shown in FIG. 3. This shows the position of the diamonds (25) and the non-diamond material (33).

We claim:

1. A method for detecting diamonds in locations which are not easily accessible, the method comprising (a) irradiating material suspected of containing diamonds in a location which is not easily accessible, with laser radiation at a pre-determined wavelength, the laser radiation being provided by irradiating means which is adapted for access to the location and the laser radiation being capable of causing Raman radiation to be scattered from diamonds in the material, (b) collecting the scattered Raman radiation by a collecting means adapted for access to the location, (c) passing the collected Raman radiation through a filtering means adapted to pass only Raman radiation characteristic of diamonds, and (d) sensing the filtered Raman radiation by a sensing means adapted to produce a signal whenever radiation characteristic of diamonds is sensed, whereby the absence or the presence of diamonds in the location is indicated.

2. A method for detecting diamonds in locations which are not easily accessible according to claim 1 in which the wavelength of the laser radiation is in the range 450 nanometers to 650 nanometers.

3. A method for detecting diamonds in locations which are not easily accessible according to claim 1 in which the irradiating means and the collecting means comprise optical fibres in the form of an integral flexible probe.

4. A method for detecting diamonds in locations which are not easily accessible according to claim 1 in which the irradiating means and the sensing means are portable.

5. A method for detecting diamonds in locations which are not easily accessible according to claim 4 in which the irradiating means and the sensing means are mounted on a vehicle.

6. A method for detecting diamonds in locations which are not easily accessible according to claim 4 in which the location is subsea.

7. A method for detecting diamonds in locations which are not easily accessible according to claim 2 in which the irradiating means and the collecting means comprise optical fibres in the form of an integral flexible probe.

8. A method for detecting diamonds in locations which are not easily accessible according to claim 5 in which the location is subsea.

9. A method for detecting diamonds in locations which are not easily accessible according to claim 8 wherein the scattered Raman radiation is passed to filtering means and sensing means located on a vessel through optical fibres.

10. A method for detecting diamonds in locations which are not easily accessible according to claim 3 wherein the location is subsea and the region in front of the probe is flushed with a fluid selected from a group consisting of water and air.

11. A method for detecting diamonds in locations which are not easily accessible according to claim 3 wherein said irradiating means includes a lens adapted to focus the laser radiation into at least one light-conducting optical fibre.

12. A method for detecting diamonds in locations which are not easily accessible according to claim 3 wherein said collecting optical fibres are adapted to pass the Raman radiation to a narrow band pass filter.

13. A method for detecting diamonds in locations which are not easily accessible according to claim 1 wherein the scattered Raman radiation is collected and filtered by a lens filter on a video camera.

14. A method for detecting diamonds in locations which are not easily accessible according to claim 1 wherein said filtering means is a narrow band pass filter.

15. A method for detecting diamonds in locations which are not easily accessible according to claim 14 wherein said filtering means comprises a glass slide having a filter coating.

* * * * *